US 6,735,316 B1

(12) United States Patent
Wurtz

(10) Patent No.: US 6,735,316 B1
(45) Date of Patent: May 11, 2004

(54) CUP-IN-A-CUP STRUCTURE AND ASSEMBLY METHOD FOR ACTIVE-NOISE-REDUCTION HEADSETS

(76) Inventor: Michael Jon Wurtz, 1156 Laurel Ave., St. Paul, MN (US) 55104

( * ) Notice: Subject to any disclaimer, the term of this patent is extended or adjusted under 35 U.S.C. 154(b) by 0 days.

(21) Appl. No.: 09/916,191

(22) Filed: Jul. 25, 2001

Related U.S. Application Data
(60) Provisional application No. 60/220,781, filed on Jul. 25, 2000.

(51) Int. Cl.[7] .................... H04R 1/10; H04R 25/00; G10K 11/16
(52) U.S. Cl. .................... 381/74; 381/71.6; 381/317
(58) Field of Search .................... 381/74, 71.6, 317, 381/324, 370.1

(56) References Cited

U.S. PATENT DOCUMENTS

| | | | |
|---|---|---|---|
| 4,160,135 A | | 7/1979 | Gorike .................... 179/182 R |
| 4,239,945 A | * | 12/1980 | Atoji et al. .................... 381/349 |
| 5,182,774 A | * | 1/1993 | Bourk .................... 379/430 |
| 5,604,813 A | * | 2/1997 | Evans et al. .............. 381/71.13 |

OTHER PUBLICATIONS

"ANR 101 Section 1: The Basics of ANR", *LightSPEED Aviation, Inc.*, http://www.lightspeed.com, pp. 1–6, (2000).
"ANR 101, A Tuturial on Active Noise Reduction", *LightSPEED Aviation, Inc.*, http://www.lightspeed.com, pp. 1–2, (2000).
Busch, M., "AVweb Product Report: LightSPEED Technologies 25XL Active Noise Reduction Headset", file://C:\TMP\%20 LightSPEED%2025XL%20ANR%20Headset.htm, pp. 1–7, (1997).

* cited by examiner

*Primary Examiner*—Forester W. Isen
*Assistant Examiner*—Elizabeth McChesney
(74) *Attorney, Agent, or Firm*—Schwegman, Lundberg, Woessner & Kluth, P.A.

(57) ABSTRACT

Some workers wear headsets to protect their hearing from loud persistent noises, such as airplane engines and construction equipment. These headsets are generally passive or active, with the active ones including ear speakers and automatic noise-reduction (ANR) circuitry to cancel or suppress certain types of loud persistent noises. One problem with active headsets concerns the difficulty of salvaging headsets that fail performance testing. Accordingly, the inventor devised a unique a unique cup-in-cup structure for the earcups of active headsets as well as related assembly and testing methods. The unique structure not only allows for pretesting of the ANR circuitry prior to assembly, but also enhances performance of the resulting headsets.

20 Claims, 5 Drawing Sheets

CUP-IN-A-CUP STRUCTURE AND ASSEMBLY METHOD FOR ACTIVE-NOISE-REDUCTION HEADSETS

CROSS-REFERENCE TO RELATED APPLICATION

This patent application is a continuation of U.S. provisional patent application No. 60/220781 filed Jul. 25, 2000 This application is incorporated herein by reference.

TECHNICAL FIELD

The present invention concerns headphones or headsets, particularly headsets with automatic noise-reduction circuitry.

BACKGROUND OF THE INVENTION

Headsets typically include two earcups which are worn over cars of users to enhance or protect their hearing. For example, many workers wear headsets to protect their hearing from loud persistent noises, such as airplane engines and construction equipment. These headsets are generally passive or active. Those that are passive only cover the ears with a sound-muffling material, whereas those that are active include ear speakers and automatic noise-reduction (ANR) circuitry. The noise-reduction circuitry cancels or suppresses certain types of noises, providing protection beyond that of passive headsets.

One problem that the present inventor recognized with active headsets, particularly those with automatic noise-reduction circuitry, concerns how they are assembled and testing. Specifically, many, if not all, conventional headsets are assembled by fitting and securing a circuit board carrying electronic circuitry into one or both of the earcups. Once assembled, the headsets undergo testing to ensure proper performance. However, the conventional earcup structure makes it difficult to remove a defective circuit board without damaging or destroying the earcup. Thus, conventional headsets or earcups that fail testing are often discarded, ultimately increasing the cost of manufacturing headsets.

Accordingly, there is a need for active headset designs and assembly techniques that facilitate testing.

SUMMARY

To address this and other needs, the inventor devised a unique cup-in-cup structure for the earcups of active headsets as well as related assembly and testing methods.

DETAILED DESCRIPTION OF PREFERRED EMBODIMENT

The following detailed description, which references and incorporates the above-identified Figures, describes and illustrates one or more specific embodiments of the invention. These embodiments, offered not to limit but only to exemplify and teach, are shown and described in sufficient detail to enable those skilled in the art to implement or practice the invention. Thus, where appropriate to avoid obscuring the invention, the description may omit certain information known to those of skill in the art.

Figure 1:
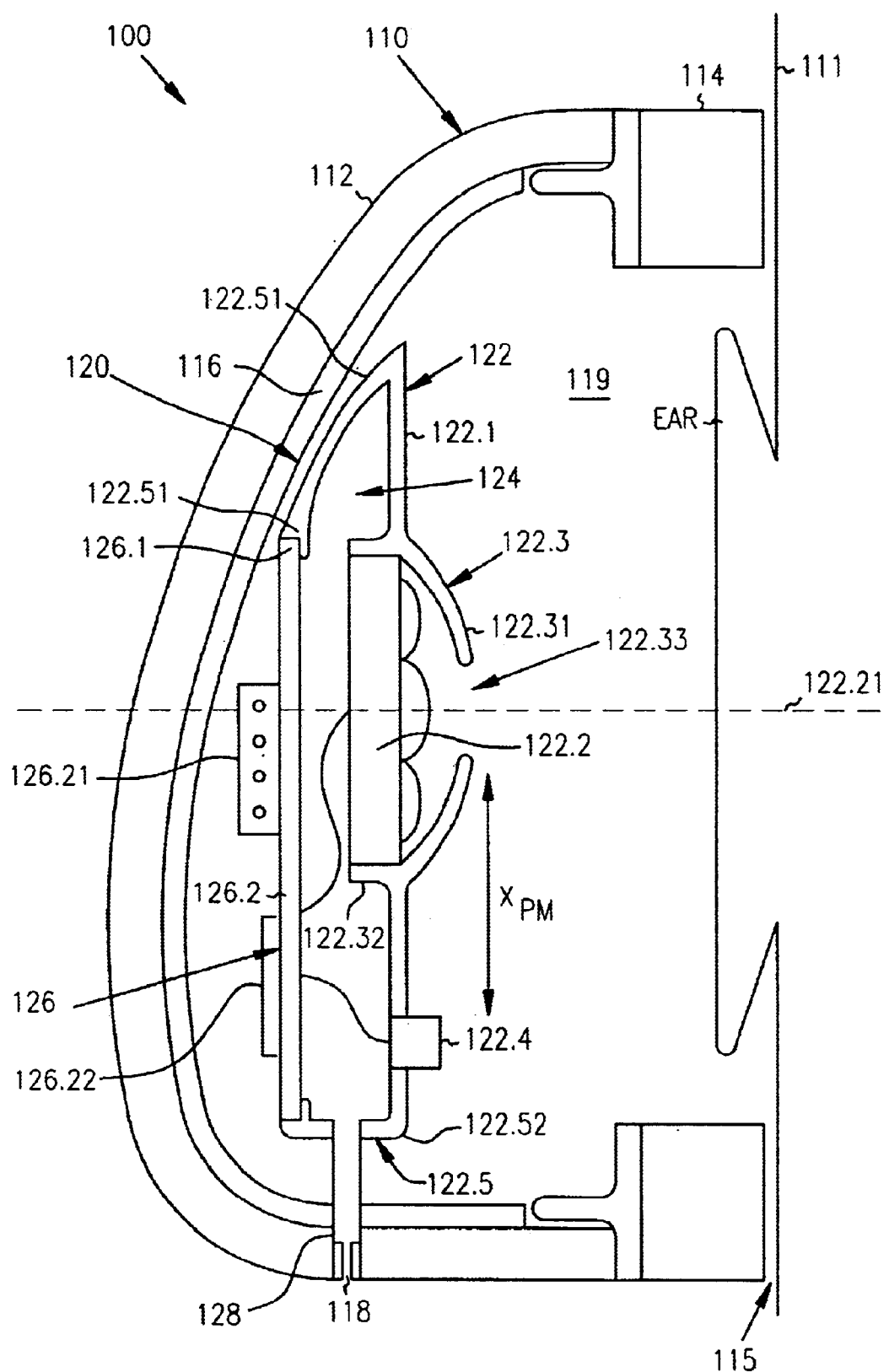
FIG. 1 is a cross-sectional view of one half of an exemplary active-noise reduction headset 100 incorporating the present invention.

FIG. 1 shows a cross-section of one half of an automatic-noise-reduction (ANR) headset, specifically an exemplary earcup 100 in accord with the present invention. Earcup 100 includes an outer-cup assembly 110 and an inner-cup assembly (or active-circuitry module) 120. (For clarity, a second earcup, and connecting bridge member are not shown.) Outer-cup assembly 110 includes an outer cup 112, an annular ear cushion 114, an acoustic-damping layer 116, a vent opening 118.

In operation, outer-cup assembly 110 fits over an ear and against the head of a user, represented generally as surface 111, defining a substantially closed front air cavity (or volume) 119. The exemplary embodiment relies on a leak 115 between ear cushion 114 and surface 111 to provide a pressure release for front cavity 119. The pressure release allows driver (122.2) to move more freely at low frequencies where the "back cavity" volume becomes stiff. This greatly increases driver efficiency greatly improving battery life and headroom. In the exemplary embodiment, the leaks exist between the cushion of the earcup and the surface of a user's head. However, other embodiments vent the front cavity of the earcup through a tube or other type passage to the outside. For example, one embodiment places a tube through the ear cushion or provides an air passage in an interface structure which mounts the cushion to the outer cup.

The exemplary embodiment of inner-cup assembly 120 provides at least two advantages. First, it can tested prior to being installed in an earcup. And second, ti can be used to augment a passive headset with an ANR function. For example, a manufacturer or end-user of passive headsets can simply acquire and an inner-cup assembly as components and install them in the earcups of passive headsets, with very little modifications. It may also be feasible to replace an inner-cup assembly in a headset with an upgraded or advanced version of the inner-cup assembly.

In particular, inner-cup assembly 120 includes a front (ear-facing) portion 122, a back cavity 124, a back portion 126, and an outlet vent or tube 128. Front portion 122 includes a planar portion 122.1, an ANR driver 122.2, a driver shroud 122.3, an ANR sensor or microphone 122.4, and side walls 122.5.

Planar portion 122.1 extends generally to engage one or more portions of the interior surface of outer cup 112 and/or acoustic damping layer 116 to facilitate holding inner-cup assembly 120 fixed relative to outer cup assembly 110. Though not shown in the Figure, the exemplary embodiment glues the inner-cup assembly into the outer cup. However, in other embodiments, the interior surface of outer cup includes one or more projections or holes which engage or mate with an interference fit with one or more corresponding holes or projections on planar portion 122.1 (or more generally inner-cup assembly 120). Some embodiments can provide extra holes or projections in the outer cup to allow for adjusting position of the inner-cup assembly within the outer cup and/or extra holes or projections on the inner-cup assembly for mating with different types of outer cups.

ANR driver (or acoustic transducer) 122.2, which defines a central driver axis 122.21, is supported within driver shroud 122.3. The present invention is not limited to any particular driver or class of drivers.

Shroud 122.3 includes a front annular flange 122.31 and a back annular flange 122.32. Front annular flange 122.31 extends forward from driver 122.2 toward surface 111 and defines a reduced driver aperture 122.33, centered on driver axis 122.21. In operation, the reduced driver aperture suppresses or mitigates cone-breakup in the driver and thus indirectly extends the cancellation bandwidth of the ANR circuitry and/or simplifies its filter requirements by suppressing or reducing the peaks of high-frequency resonances. Additionally, the inner-cup assembly itself damps the outer cup by providing a constrained layer between the inner and outer cup, improving attenuation of high frequencies.

In the exemplary embodiment, aperture 122.33 is circular; however, in other embodiments, flange 122.31 has multiple fingers that define the aperture as a starlike opening. Some embodiments may augment aperture 122.33 with holes distributed around the aperture. And still other embodiments may replace aperture 122.33 with a set of holes concentrated around the driver axis or distributed uniformly across a dome or other structure covering the driver. In general, it is believed that any driver-shroud structure that presents a reduced view of driver 122.2 lies within the scope of the invention.

In addition to front annular flange 122.31, driver shroud 122.3 includes back annular flange 122.32. Back annular flange 122.32 projects perpendicularly from planar portion 122.1 of front portion 122, surrounding and engaging ANR driver 122.2.

In other embodiments, the back annular flange consists of a set of two or more annular flange segments or spaced fingers that impinge on and thus secure the driver in place. However, some embodiments glue, screw, or otherwise secure the driver to front portion 122. Still other embodiments may form a driver having an integral or non-integral structure for providing a reduce aperture and/or serving the function of planar portion 122.1. Thus, the present invention is not limited to any particular frontal structure.

In addition to planar portion 122.1, ANR driver 122.2, and driver shroud 122.3, front portion 122 also includes an ANR sensor or microphone 122.4.

ANR sensor 122.4, for example, an electret microphone, is mounted in or on planar portion 122.1 a distance $X_{DM}$ from central driver axis 122.21. Distance $X_{DM}$ is chosen using known principles for making and using ANR headsets.

Sidewall 122.5 which extends back from planar portion 122.1 to engage back portion 126, thereby defining back cavity 124. More specifically in the exemplary embodiment, sidewall 122.5 extends back from planar portion 122.1 toward central driver axis 122.21 to define a surface in general conformity with adjacent portions of outer cup 112. Sidewall 122.5 terminates with an annular shelf or rim 122.51 that engages a peripheral or perimeter face 126.1 of back portion 126.

As shown in the figure, the exemplary embodiment provides an upper portion 122.51 of sidewall 122.5 with a different contour than that of its lower portion 122.52. However, other embodiments can provide a sidewall with a uniform contour. Additionally, other embodiments may omit all or one or more portions of the sidewall from front portion 122 and add a complete sidewall or one or more sidewall portions to back portion. For example, some embodiments may provide the front and back portions each with complete peripheral sidewalls that engage each other to define the back cavity, in roughly the fashion of two hemispheres engaged to form a sphere. Or, some embodiments may provide the front and back portions with sidewall segments that mate in an interleaved or "interdigitated" manner to define the back cavity. Additionally, some embodiments define the back cavity by sizing planar portion 122.1 to effectively partition the interior volume of earcup into acoustically separate volumes, thereby obviating engagement of the front portion with the back portion. This can be done by extending the planar portion to contact the acoustic damping layer. (In some variants of this embodiment, the planar portion would include a channel covered by another planar member to form an air passage that mates with vent opening 118. This air passage could be tapered and/or filled with foam or other to restrict air flow. ) In general, it is believed that the invention is not limited to any particular structure for defining the back cavity.

Back portion 126 includes a circuit board 126.2. Circuit board 126.2 includes a connector 126.21 and circuitry 126.22. Although the exemplary embodiment includes circuitry 126.22 in the form of ANR circuitry, other embodiments may also provide a variety of other circuits, such as wireline or wireless communication circuits.

Outlet vent or tube 128 extends from vent opening 118 in outer cup through an opening 122.53 in sidewall 122.5 of front portion 122. In this exemplary embodiment, the vent comprises a tube 128.1 with a restrictive opening 128.2. The restrictive opening provides a significant resistive component which, if made sufficiently large, prevents the inductance of the tube from resonating with the the back cavity. Such resonance will add significant impedance to the back of the driver and cause system response to dip. Tube resistance can be increased, for example, by tapering the tube and/or inserting screen, foam, or other flow restriction into it. The vent tube provides a pressure release from the back of the driver without venting to the inside cup. For aviation applications, this release allows for ambient pressure changes experienced when a plane changes altitudes.

Figure 2:
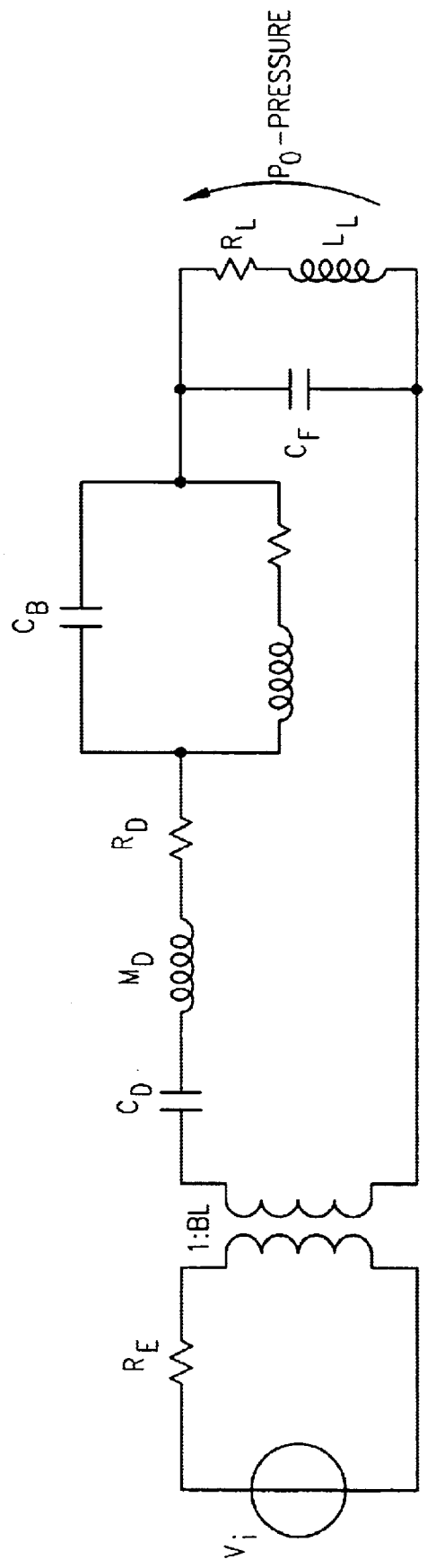
FIG. 2 is a schematic diagram of an equivalent electric circuit for the acoustic structure of headset 100.
Figure 3:
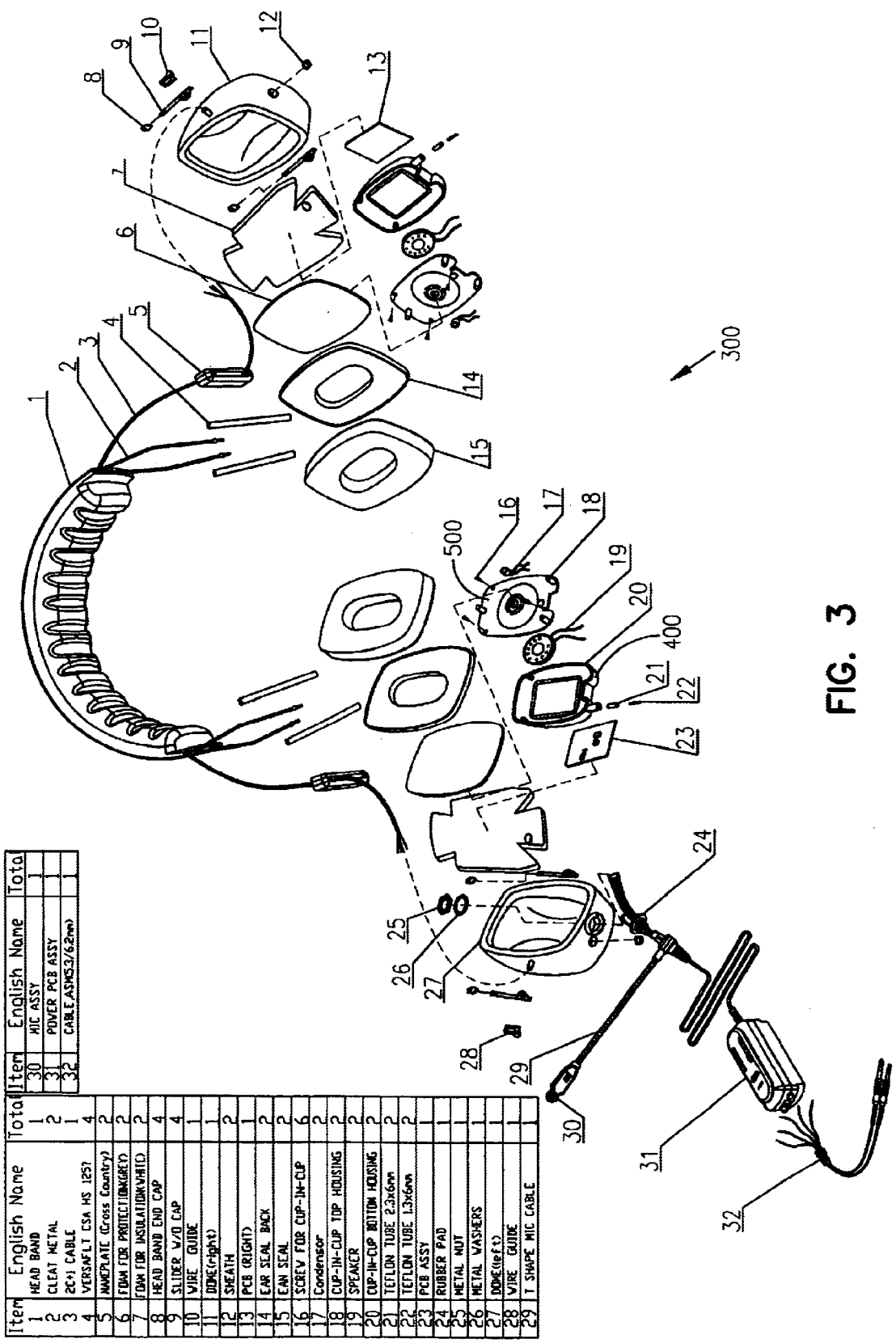
FIG. 3 is an exploded view of an exemplary active-noise-reduction headset 300 incorporating teachings of the present invention.
Figure 4:
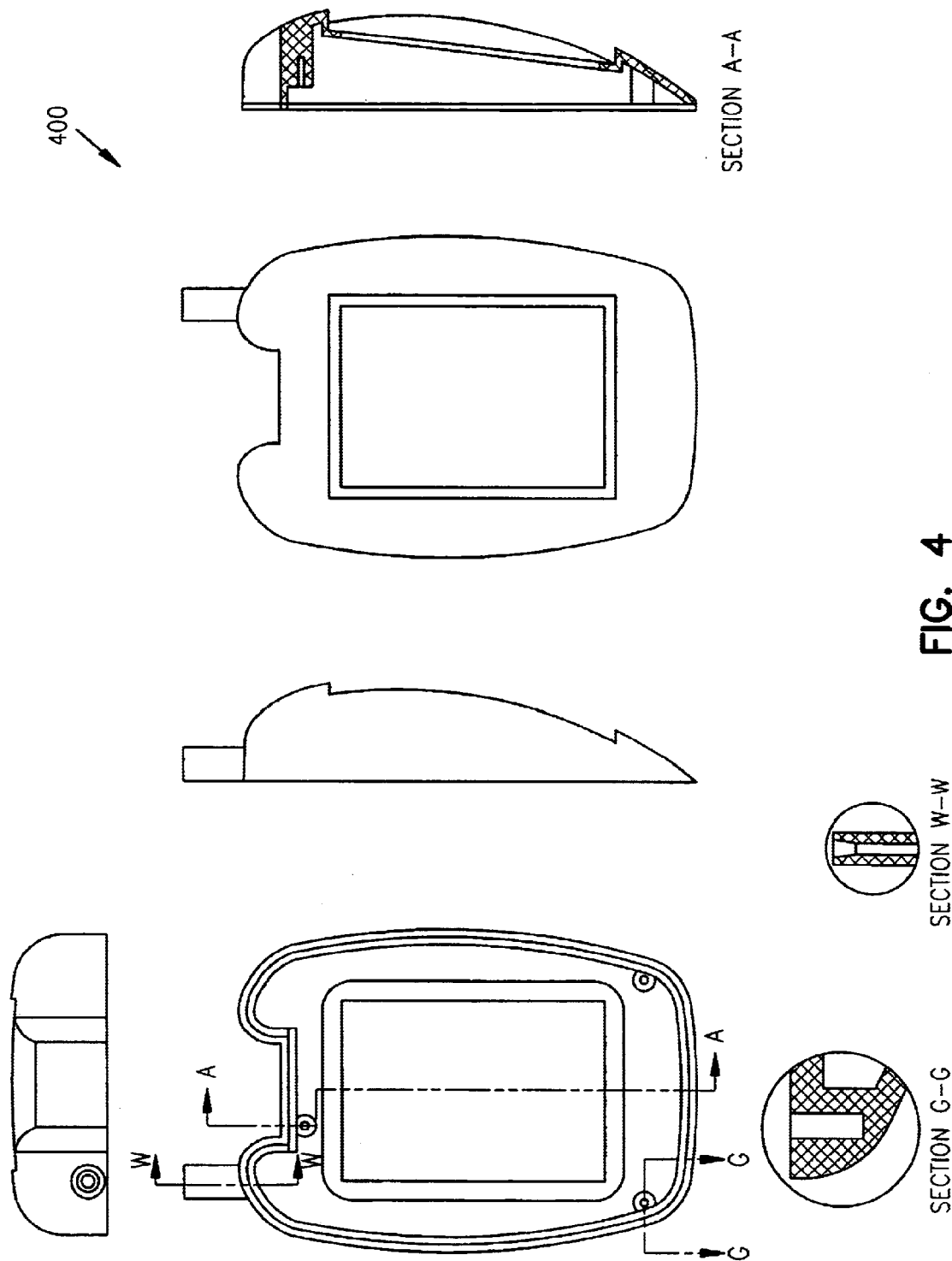
FIG. 4 includes front, side, and back views of a bottom housing shown in FIG. 3.
Figure 5:
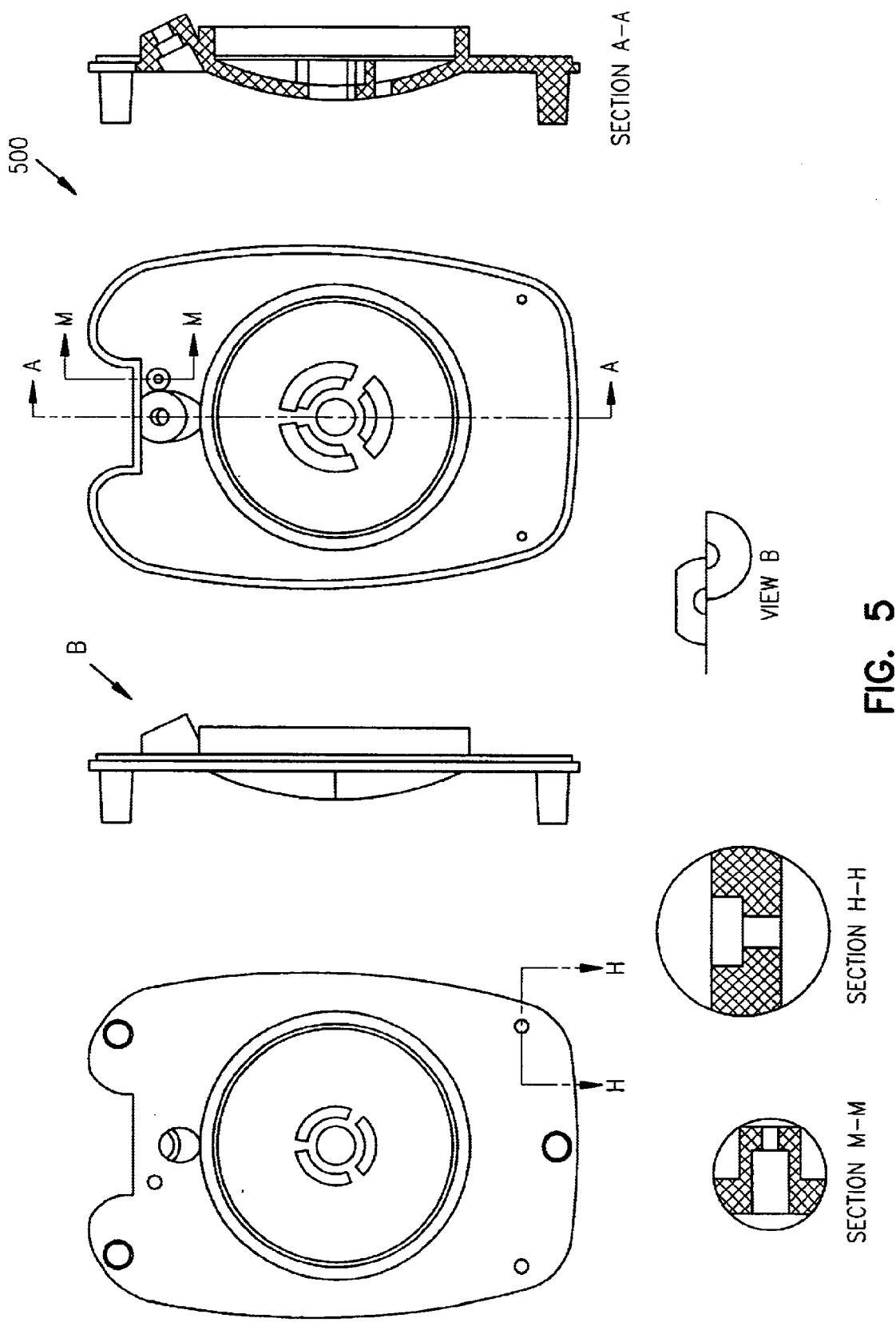
FIG. 5 includes front, side, and back views of a top housing shown in FIG. 3.

FIG. 2 shows a simplified equivalent electric circuit 200 for the acoustics of exemplary earcup 110 in FIG. 1. Circuit 200 includes:

capacitor $_D$ which represents ANR driver compliance;
inductor $M_D$ which represents mass of the ANR driver;
resistor $R_D$ which represents damping of the ANR driver;
resistor $R_F$ which represents voice coil resistance of the ANR driver;
transformer ratio 1:BL which represents force factor of the driver;
capacitor $C_B$ represents compliance of the back cavity;
inductor $L_V$ represents the vent
resistor $R_V$ represents the vent
$C_F$ is the compliance of the front cavity
$L_L$ is the inductance of leaks around the seal
$R_L$ is the resistance of leaks around the seal.

This simplified equivalent circuit provides the following insights regarding size and placement of vent 128. If resistor $R_V$ the restriction of vent 128 from the inner-cup assembly, is small, then at the resonance frequency of $L_V$ and $C_B$, which respectively represent the vent inductance and back-cavity compliance, the impedance will become infinite. Thus, it is desirable to make resistor $R_V$ sufficiently large to provide a damping effect. On the other hand, if the vent is closed, the driver must overcome the stiffness of the back cavity, causing a significant loss in efficiency. And, if the vent outlets to the front cavity, rather than outside the earcup, it will act, at low frequencies, as a short across capacitors $C_B$ and $C_F$, greatly reducing the output efficiency of the driver.

CONCLUSION

In furtherance of the art, the inventor has presented one or more embodiments of active headsets a unique cup-in-cup structure and partitioning structure for the earcups of active headsets as well as related assembly and testing methods.

The embodiments described above are intended only to illustrate and teach one or more ways of practicing or implementing the present invention, not to restrict its breadth or scope. The actual scope of the invention, which encompasses all ways of practicing or implementing the concepts of the invention, is defined by the following claims and their equivalents.

What is claimed is:

1. An active-noise-reduction headset comprising:
   a first earcup for defining a first air cavity when engaged with a head of a user; and
   an enclosure defining a second air cavity within the first air cavity; and
   an air passage coupling the second air cavity to an environment exterior to the first earcup when engaged with the head of the user.

2. The active-noise-reduction headset of claim 1, wherein the enclosure comprises a printed circuit board carrying active-noise-reduction circuitry.

3. The active-noise-reduction headset of claim 1, wherein the air passage has a length and is tapered along the length.

4. The active-noise-reduction headset of claim 1, wherein the air passage comprises a tubular structure filled with foam.

5. An active-noise-reduction headset comprising:
   a first for defining a first air cavity when engaged with a head of a user;
   an enclosure defining a second air cavity within the first air cavity; and
   means for equalizing pressure within the second air cavity and pressure external to the first earcup when engaged with the head of the user.

6. The active-noise-reduction headset of claim 5, wherein the enclosure comprises an ANR driver.

7. The active-noise-reduction headset of claim 6, wherein the ANR driver has an axis and a first aperture centered on the axis, and wherein the enclosure includes an annular flange member having a second aperture centered on the axis, with the second aperture defining an area less than that of the first aperture.

8. The active-noise-reduction headset of claim 5, wherein the enclosure comprises a printed circuit board and an ANR driver, with the printed circuit board defining at least a portion of a back surface of the enclosure and the ANR driver defining at least a portion of a front surface of the enclosure.

9. An active-noise-reduction headset comprising:
   a first earcup for defining a first air cavity when engaged with a head of a user; and
   an enclosure defining a second air cavity within the first air cavity; and
   means for reducing pressure in the second air cavity when the first earcup is engaged with the head of the user.

10. The active-noise-reduction headset of claim 9:
    wherein the first air cavity includes a front cavity;
    wherein the enclosure includes an ANR driver which confronts the front cavity; and
    wherein at least a portion of the front cavity is between the enclosure and the head of a user when the first earcup is engaged.

11. A method of making an active-noise-reduction headset, comprising:
    providing a headset having at least one earcup for defining a first air cavity against the head of a user; and
    mounting an active-noise-reduction module into the one earcup, the active-noise-reduction module comprising an enclosure defining a second air cavity, with at least a surface portion of the enclosure formed by an active-noise-reduction driver and another surface portion of the enclosure formed by a printed circuit board carrying acoustic-noise-reduction circuitry.

12. The method of claim 11, wherein the one earcup of the headset includes a vent opening; and wherein mounting the active-noise-reduction module into the one earcup, comprises coupling the second air cavity to the vent opening.

13. The method of claim 11, wherein the active-noise-reduction driver has an aperture and wherein the module further includes means for reducing the aperture.

14. An active-noise-reduction module for use in headsets, the module comprising:
    an enclosure defining an air cavity;
    a printed circuit board including electronic circuitry and forming a surface portion of the enclosure; and
    an active-noise-reduction driver forming another surface portion of the enclosure.

15. The module of claim 14, wherein the active-noise-reduction driver has an aperture and wherein the module further includes means for reducing the aperture.

16. An active-noise-reduction module for installation in an earcup of a headset, the module comprising:
    a structure carrying active-noise-reduction circuitry;
    an active-noise-reduction driver;
    means for holding the structure and the active-noise-reduction driver and defining an acoustic cavity therebetween; and
    means for equalizing pressure within the acoustic cavity and pressure external to the earcup when engaged with a user's head.

17. The active-noise-reduction module of claim 16, wherein the structure comprises a printed circuit board.

18. The active-noise-reduction module of claim 16, further comprising;
    a microphone coupled to the active-noise-reduction circuitry; and
    wherein the means for holding the structure and the active-noise-reduction driver also holds the microphone.

19. The active-noise-reduction module of claim 16, further comprising means for mounting the means for holding to the earcup.

20. The active-noise-reduction module of claim 16:
    wherein the acoustic-noise-reduction driver has an associated aperture; and
    wherein the module further comprises means for reducing the aperture of the driver.

* * * * *

UNITED STATES PATENT AND TRADEMARK OFFICE
CERTIFICATE OF CORRECTION

PATENT NO. : 6,735,316 B1 Page 1 of 1
APPLICATION NO. : 09/916191
DATED : May 11, 2004
INVENTOR(S) : Wurtz It is certified that error appears in the above-identified patent and that said Letters Patent is hereby corrected as shown below:

In column 5, line 33, in Claim 5, insert -- earcup -- before "for".

Signed and Sealed this

Twentieth Day of March, 2007

JON W. DUDAS
*Director of the United States Patent and Trademark Office*